(12) United States Patent
Wang

(10) Patent No.: US 10,426,368 B2
(45) Date of Patent: Oct. 1, 2019

(54) METHOD AND SYSTEM FOR CARDIAC ISCHEMIA DETECTION

(71) Applicant: KONINKLIJKE PHILIPS N.V., Eindhoven (NL)

(72) Inventor: Jyh-Yun John Wang, Newton, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 575 days.

(21) Appl. No.: 14/371,461

(22) PCT Filed: Jan. 14, 2013

(86) PCT No.: PCT/IB2013/050319
§ 371 (c)(1),
(2) Date: Jul. 10, 2014

(87) PCT Pub. No.: WO2013/111031
PCT Pub. Date: Aug. 1, 2013

(65) Prior Publication Data
US 2015/0011902 A1   Jan. 8, 2015

Related U.S. Application Data

(60) Provisional application No. 61/590,999, filed on Jan. 26, 2012, provisional application No. 61/660,840, filed on Jun. 18, 2012.

(51) Int. Cl.
*A61B 5/044* (2006.01)
*A61B 5/0452* (2006.01)
(Continued)

(52) U.S. Cl.
CPC ........... *A61B 5/044* (2013.01); *A61B 5/0452* (2013.01); *G06F 19/321* (2013.01); *G16H 40/63* (2018.01)

(58) Field of Classification Search
CPC .............................. A61B 5/044; A61B 5/0452
See application file for complete search history.

(56) References Cited

U.S. PATENT DOCUMENTS

| 7,925,337 B2 | 4/2011 | Rajagopalan et al. |
| 8,060,193 B2 | 11/2011 | Rajagopalan et al. |

(Continued)

FOREIGN PATENT DOCUMENTS

| WO | 2006033038 A2 | 3/2006 |
| WO | 2010037400 A1 | 4/2010 |

(Continued)

OTHER PUBLICATIONS

Sangkachand et al, "Continuous ST-Segment Monitoring: Nurses' Attitudes, Practices, and Quality of Patient Care", American Journal of Critical Care, May 2011.*

(Continued)

*Primary Examiner* — George R Evanisko

(57) ABSTRACT

Disclosed herein are methods and systems providing improvements enhancing speed and accuracy in interpreting the electrocardiogram (ECG) for ischemia identification using a graphical presentation. An ischemia criteria and ST segment measurements to be tested are graphically presented simultaneously. The graphical presentation allows the violation of the ischemia criteria to be visualized without any ambiguity. To further ensure that such a condition will not be overlooked, additional graphical highlighting is provided. This graphical approach can be used to improve the detection of conditions that fulfill the specified ischemia criteria and reduce the variation of individual interpretation for patients with border-line ST segment changes.

19 Claims, 15 Drawing Sheets

(51) Int. Cl.
*G06F 19/00* (2018.01)
*G16H 40/63* (2018.01)

(56) References Cited

U.S. PATENT DOCUMENTS

| | | | |
|---|---|---|---|
| 8,396,544 B2* | 3/2013 | Rajagopalan | A61B 5/0452 600/523 |
| 2007/0010753 A1* | 1/2007 | MacAdam | A61B 5/04525 600/523 |
| 2010/0210961 A1* | 8/2010 | Rajagopalan | A61B 5/0452 600/523 |
| 2010/0238192 A1* | 9/2010 | Kouchi | A61B 5/044 345/593 |
| 2010/0249622 A1 | 9/2010 | Olson | |
| 2011/0060234 A1 | 3/2011 | Zhou et al. | |
| 2011/0184692 A1 | 7/2011 | Andersen | |
| 2012/0041328 A1* | 2/2012 | Rajagopalan | A61B 5/0452 600/523 |
| 2012/0323133 A1* | 12/2012 | Lindauer | A61B 5/04011 600/523 |

FOREIGN PATENT DOCUMENTS

| | | | |
|---|---|---|---|
| WO | 2010099386 A1 | | 9/2010 |
| WO | WO2010/099386 | * | 9/2010 |

OTHER PUBLICATIONS

Antman et al: "2007 Focused Update of the ACC/AHA 2004 Guidelines for the Management of Patients With ST-Elevation Myocardial Infarction"; Journal of the American College of Cardiology, 2008, vol. 51, No. 2, pp. 210-247.

Drew et al: "Practice Standards for Electrocardiographic Monitoring in Hospital Settings"; Circulation, 2004;vol. 110, pp. 2721-2746.

Thygesen et al: "Universal Definition of Myocardial Infarction"; Journal of the American College of Cardiology, 2007, vol. 50, No. 22, pp. 2195.

Goldman: "Principles of Clinical Electrocardiography"; Lang Medical Publications, 1970, pp. 9-13.

2005 International Consensus Conference Part 5: Acute Coronary Syndromes; 2005; Circulation; 112:III-55-III-72.

Antman, E. M., et al.; 2007 Focused Update of the ACC/AHA 2004 Guidelines for the Management of Patients with ST-Elevation Myocardial Infarction; 2008; Circulation; 117:296-329.

Gregg, R. E., et al.; Computerized classification of proximal occlusion in the left anterior descending coronary artery; 2010; J. of Electrocardiology; 43:634-639.

Kligfield, P., et al.; Recommendations for the Standardization and Interpretation of the Electrocardiogram: Part I; 2007; Circulation; 115:1306-1324.

Nimmermark, M. O., et al.; The impact of numeric and graphic displays of ST-segment deviation levels on cardiologists' decisions of reperfusion therapy for patients with acute coronary occlusion; 2011; J. of Electrocardiology; 44:502-508.

Rautaharju, P. M., et al.; AHA/ACCF/HRS Recommendations for the Standardization and Interpretation of the Electrocardiogram, Part IV; 2009; Circulation; 119:e241-e250.

Sangkachand, P., et al.; Continuous ST-Segment Monitoring: Nurses' Attitudes, Practices, and Quality of Patient Care; 2011; American Journal of Critical Care; 20(3)226-237.

Thygesen, K., et al.; Universal Definition of Myocardial Infarction; 2007; Circulation; 116:2634-2653.

Wagner, G. S., et al.; AHA/ACCF/HRS Recommendations for the Standardization and Interpretation of the Electrocardiogram: Part VI; 2009; Circulation; 119:e262-e270.

* cited by examiner

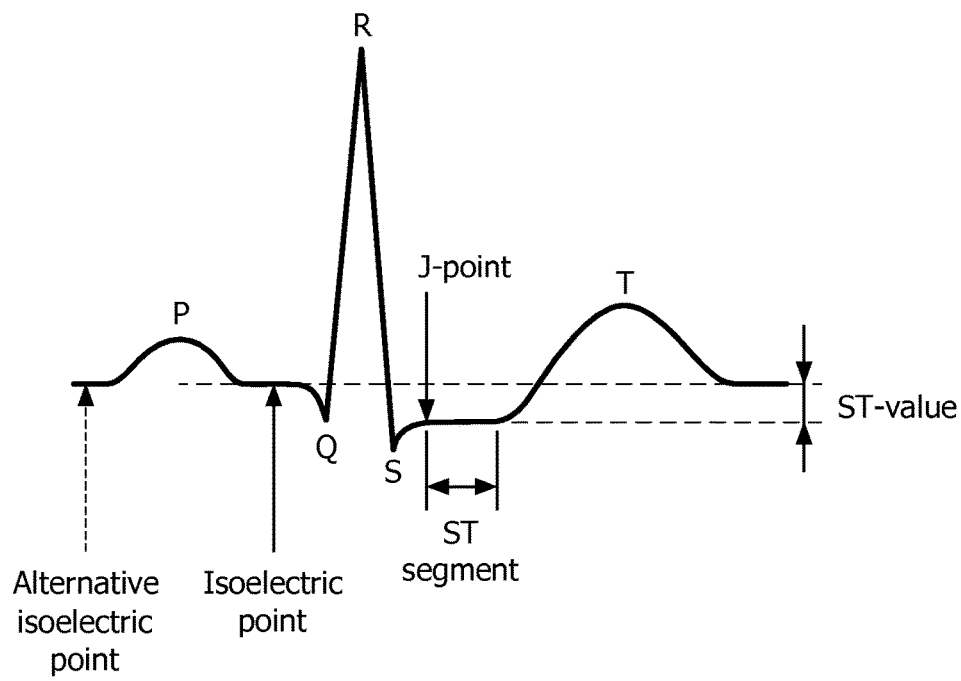
FIG. 1
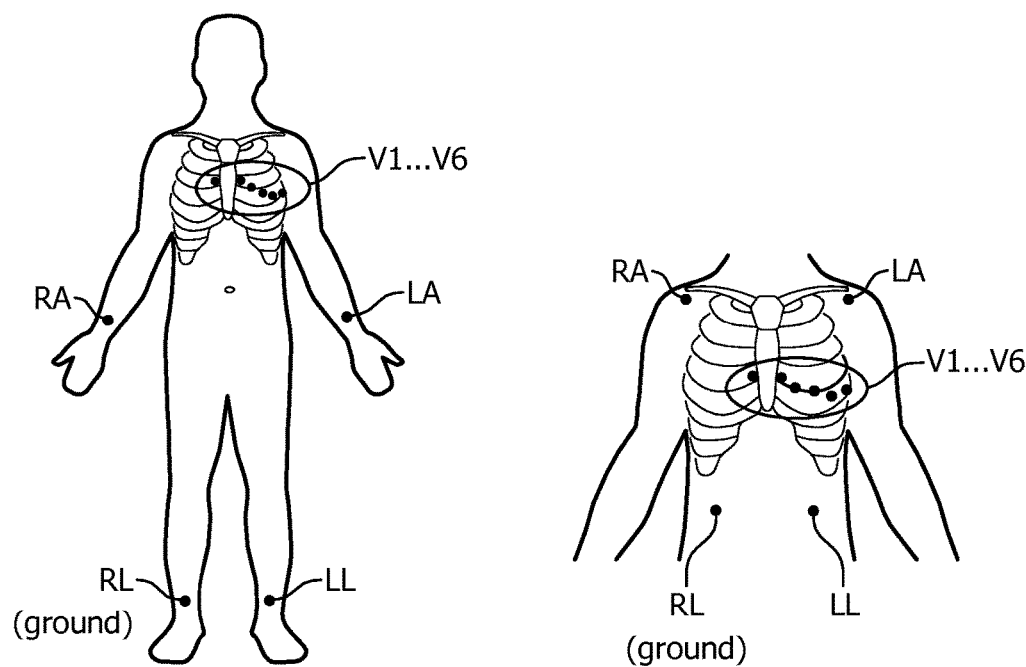
FIG. 2
FIG. 3

FIG. 4-I

| FIG. 4-I | FIG. 4-II |

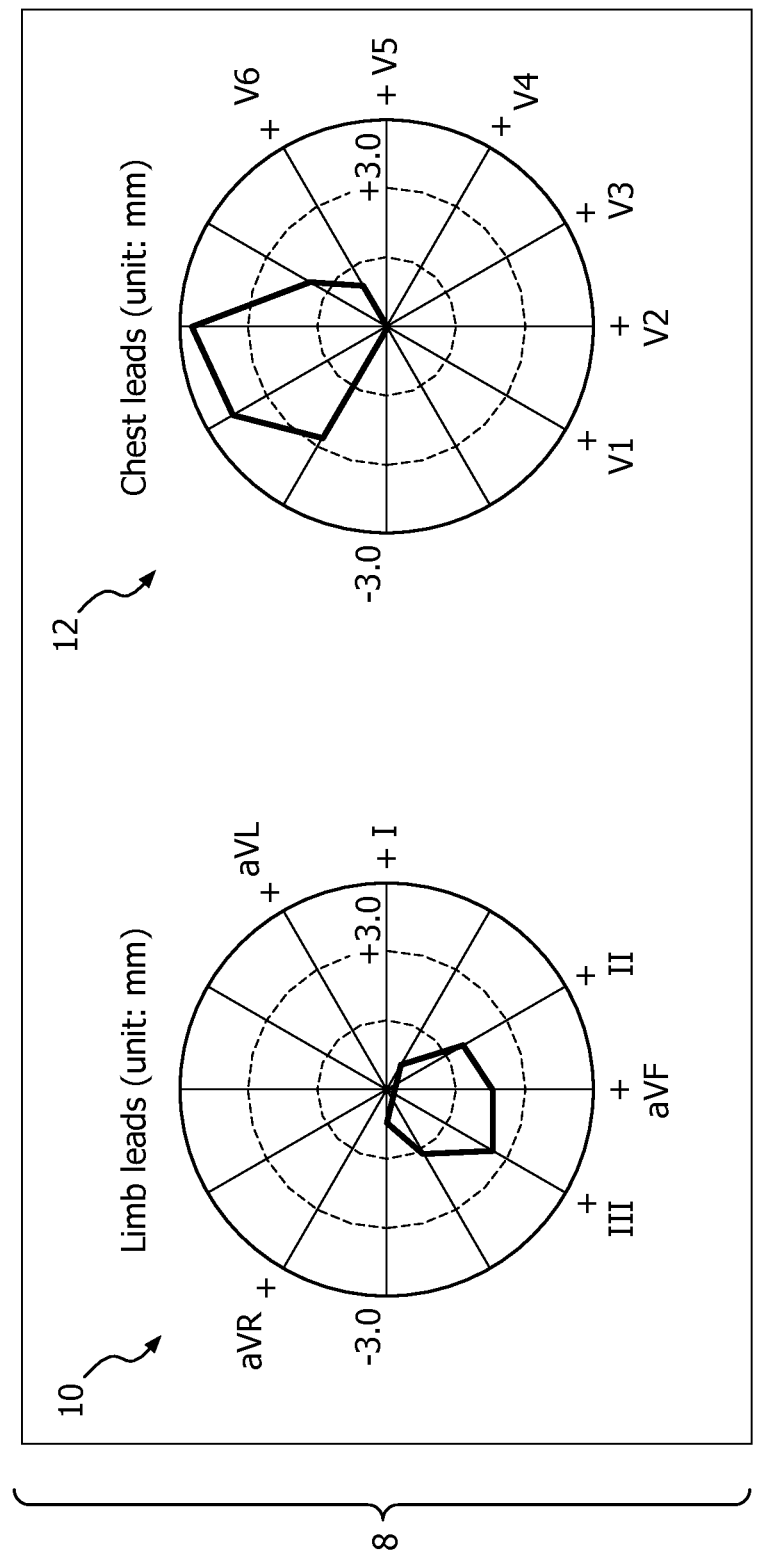
FIG. 4-II

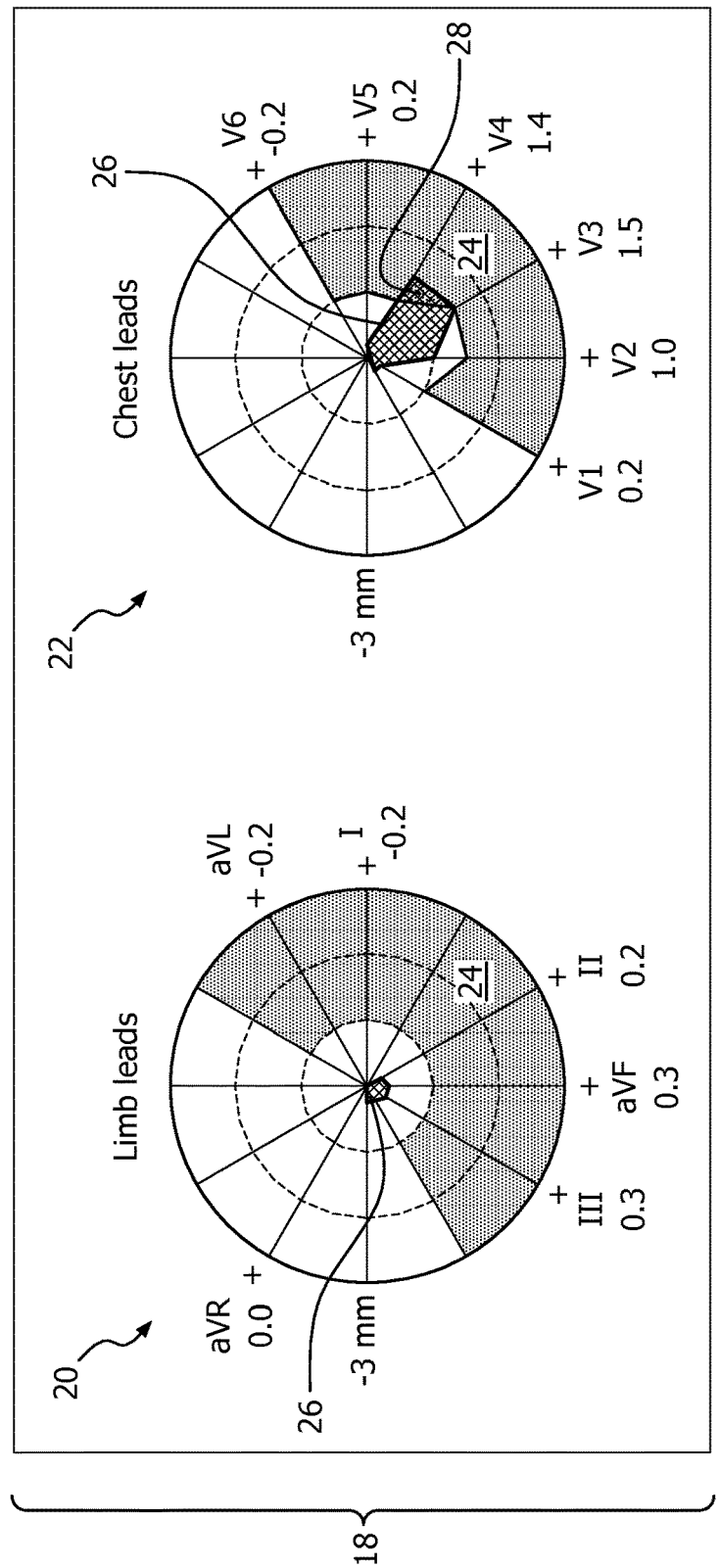
FIG. 5-II

METHOD AND SYSTEM FOR CARDIAC ISCHEMIA DETECTION

CROSS REFERENCE TO RELATED APPLICATIONS

This application is a national filing of PCT application Serial No. PCT/IB2013/050319, filed Jan. 14, 2013, published as WO 2013/111031 A 1 on Aug. 1, 2013, which claims the benefit of U.S. provisional application Ser. No. 61/590,999 filed Jan. 26, 2012 and U.S. provisional application Ser. No. 61/660,840 filed Jun. 18, 2012, both of which are incorporated herein by reference.

The following relates to the cardiology arts, emergency medical treatment arts, medical instrumentation arts, and related arts.

The electrocardiogram (ECG) is a graphic recording of the electrical potentials generated by the electrical activity in the heart. The electrical impulse formation and conduction associated with each cardiac contraction produce weak electrical currents that spread through the entire body. By applying electrodes to various positions on the body and connecting these electrodes to an electrocardiographic apparatus, the variation in the magnitude of the electrical potential is recorded. The magnitude of the recorded ECG is usually in the order of millivolts.

ECG is ubiquitous in urgent care settings such as hospital emergency rooms, ambulances, and the like. ECG is a noninvasive technique capable of providing fast assessment of cardiac activity, and can yield substantial information when analyzed by a skilled cardiologist. An urgent care setting, however, calls for treating medical personnel to make rapid decisions regarding critical patient care, and sometimes without the benefit of an available on-call cardiologist. Professional organizations such as the American College of Cardiology Foundation (ACCF), American Heart Association (AHA), and European Society of Cardiology (ESC) have developed heuristic guidelines for assessing ECG in the urgent care setting. These guidelines enable medical personnel to make fast and effective decisions based on the ECG data. For patients presenting with obvious abnormal ECGs that meet the guidelines, no further decision support is needed. However, for patients with less definitive ECG changes, misinterpretation of the ECG by treating medical personnel can lead to diagnostic error and consequent non-optimal patient treatment.

The following discloses improvements that enhance the accuracy in interpreting the electrocardiograph (ECG) for ischemia identification using a graphical presentation.

According to one aspect, an apparatus comprises an electronic data processing device configured to generate and display an ST Map plotting ST values and superimpose on the ST Map a rendering of an ischemia criteria area representing an ischemia criteria. The electronic data processing device may optionally be further configured to determine whether ST values of the ST Map satisfy the ischemia criteria, and if so to compute and highlight on the ST Map an overlapping region between (1) an ST area delineated by the ST values of the ST Map and (2) the ischemia criteria area.

According to another aspect, a method comprises: computing a polygonal ST area in a plane, the polygonal ST area having vertices defined by measured ST values on axes representing electrocardiograph leads, wherein the computing is performed by an electronic data processing device; and displaying a rendering of the polygonal ST area in the plane together with an ischemia criteria area representing an ischemia criteria in the plane. The method optionally further comprises: determining whether the measured ST values satisfy the ischemia criteria wherein the determining is performed by the electronic data processing device; and conditional upon determining that the measured ST values satisfy the ischemia criteria, highlighting an overlapping region between the polygonal ST area and the ischemia criteria area in the rendering.

According to another aspect, a non-transitory storage medium stores instructions executable by an electronic data processing device to perform a method including: computing a frontal polygonal ST area in a frontal plane wherein the frontal polygonal ST area has vertices defined by measured ST values on axes representing electrocardiograph limb or augmented leads; computing a transverse polygonal ST area in a transverse plane wherein the transverse polygonal ST area has vertices defined by measured ST values on axes representing electrocardiograph precordial leads; displaying a frontal plane graphic presentation including the frontal polygonal ST area and an ischemia criteria area representing the ischemia criteria in the frontal plane; and displaying a transverse plane graphic presentation including the transverse polygonal ST area and an ischemia criteria area representing the ischemia criteria in the transverse plane. Optionally, the method further includes: determining whether the measured ST values satisfy the ischemia criteria, and, conditional upon determining that the measured ST values satisfy the ischemia criteria, highlighting an overlapping region between at least one of (1) the front polygonal ST area and the ischemia criteria area representing the ischemia criteria in the frontal plane and (2) the transverse polygonal ST area and the ischemia criteria area representing the ischemia criteria in the transverse plane.

One advantage resides in increased speed in diagnosing and treating cardiac ischemia in urgent care settings.

Another advantage resides in increased accuracy in diagnosing and treating cardiac ischemia in urgent care settings.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIG. 1 diagrammatically shows one cardiac cycle of ECG data with selected quantities indicated by annotations.

FIGS. 2 and 3 show illustrative electrode layouts for 12-lead ECG and a modified (Mason-Likar) 12-lead ECG, respectively.

Figure 15:
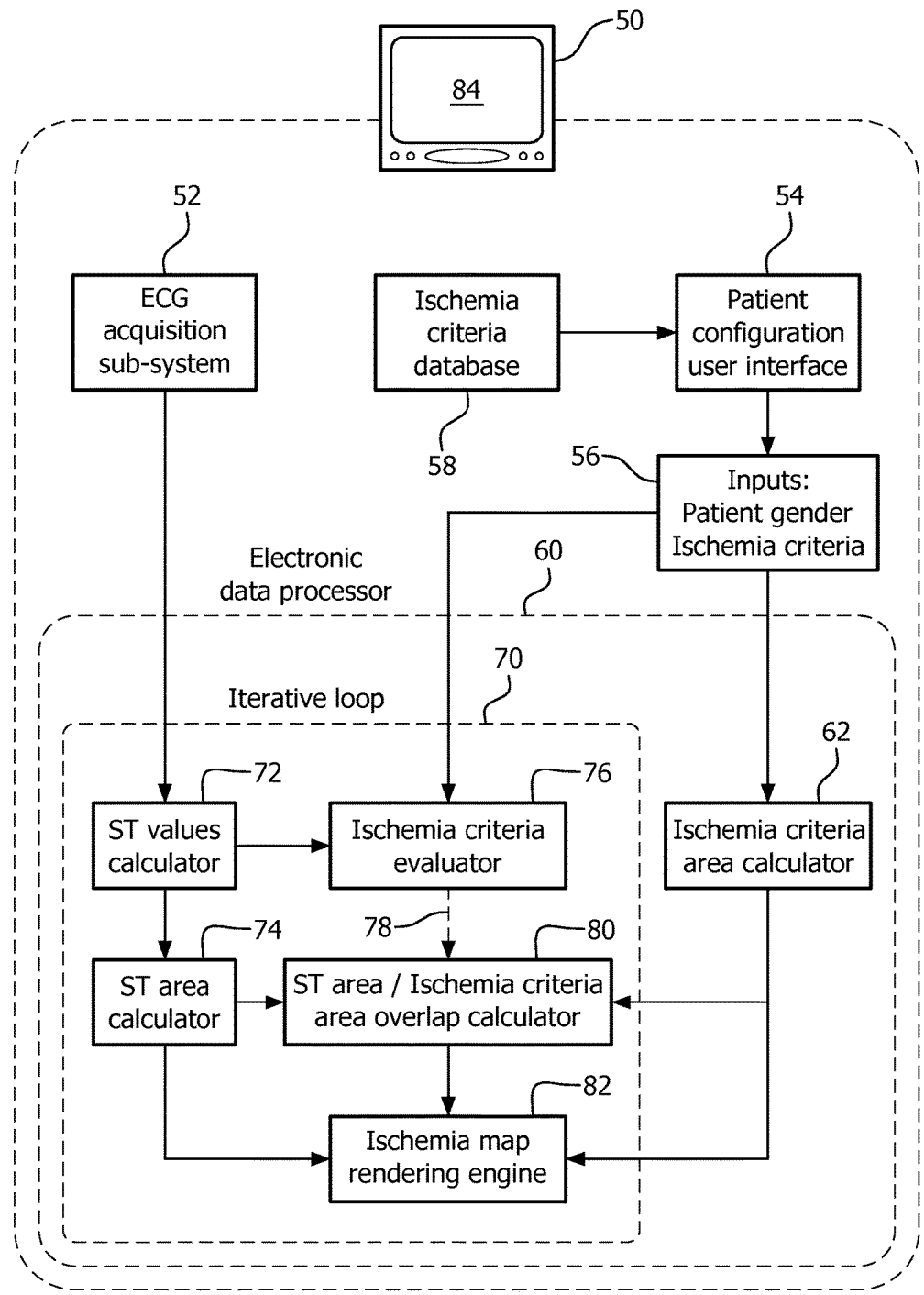

FIG. 15 diagrammatically shows an instrument for performing a cardiac ischemia detection technique as disclosed herein.

With reference to FIG. 1, a typical ECG includes a series of waves, which are repeated with each cardiac cycle. These waves are labeled as P, QRS, and T according to convention. The P-wave represents the depolarization and contraction of both atria, the QRS complex represents the depolarization and contraction of the ventricles, and the T-wave represents the repolarization of the ventricles.

With reference to FIG. 2, an ECG is typically measured using a standard 12-lead ECG (see, e.g., Kligfield et al., "AHA/ACC/HRS Recommendations for the Standardization and Interpretation of the Electrocardiogram Part I: The Electrocardiogram and Its Technology", Circulation vol. 115, pages 1306-24 (2007)). As shown in FIG. 2, 10 electrodes are used to acquire the 12-lead ECG. Three electrodes are placed on the limbs, namely: a right arm (RA) electrode, a left arm (LA) electrode, and a left leg (LL) electrode. Six additional electrodes are placed on the chest (V1 to V6), and a ground reference electrode is placed on the right leg (RL), although more generally the ground electrode can be placed anywhere on the patient. In order to obtain a specific precordial lead, a chest electrode must be placed in the appropriate location.

TABLE 1

Standard 12-Lead ECG

| Lead | Type | Lead Calculation |
|------|------|------------------|
| I | Limb | LA-RA |
| II | Limb | LL-RA |
| III | Limb | LL-LA |
| aVR | Augmented | RA-(LA + LL)/2 |
| aVL | Augmented | LA-(RA + LL)/2 |
| aVF | Augmented | LL-(RA + LA)/2 |
| V1 | Precordial | V1-(RA + LA + LL)/3 |
| V2 | Precordial | V2-(RA + LA + LL)/3 |
| V3 | Precordial | V3-(RA + LA + LL)/3 |
| V4 | Precordial | V4-(RA + LA + LL)/3 |
| V5 | Precordial | V5-(RA + LA + LL)/3 |
| V6 | Precordial | V6-(RA + LA + LL)/3 |

The 12 ECG leads are defined as follows. There are three limb leads (I, II, and III), three augmented limb leads (aVR, aVL, and aVF), and six precordial leads (V1 to V6). Table 1 shows how these 12 leads are derived from the nine electrodes. Each of the three limb leads (I, II, III) represents a difference of electrical potential between two selected sites. Each of the three augmented limb leads (aVR, aVL, aVF) records the electrical potential at one extremity with reference to (the average of) the other two remaining extremities. These six limb leads record the electrical potentials in the frontal plane. Also note that the six frontal plane leads are not independent. In the 12-lead configuration, there are two independent signal channels from three limb electrodes.

The precordial V leads record the electrical potential at the specific chest locations with reference to the three extremities. Each precordial lead records the electrical potential in the horizontal plan as viewed from the selected electrode placement site. In addition to the six standard chest leads, additional chest leads are often used in the investigation of ischemia. They include four right-side chest leads (V3R, V4R, V5R, and V6R) and three posterior leads (V7, V8, and V9).

Although the placement of the standard limb electrodes is not a problem for acquiring resting 12-lead ECG, it can be impractical for ambulatory applications such as continuous monitoring or exercise testing. Not only is the positioning of the standard limb electrodes inconvenient and uncomfortable for the patient, but the limb electrodes are also highly susceptible to measurement artifacts due to patient movement of the limbs.

With reference to FIG. 3, for ambulatory applications a modified electrode configuration (Mason-Likar) is sometimes used (see, e.g., Kligfield et al., "AHA/ACC/HRS Recommendations for the Standardization and Interpretation of the Electrocardiogram Part I: The Electrocardiogram and Its Technology", Circulation vol. 115, pages 1306-24 (2007)). In this modified configuration, the three limb electrodes (LA, RA, LL) and the ground electrode (RL when the right leg is used as the ground location) are placed on the torso as shown in FIG. 3.

It is also possible to derive the 12-lead ECG from fewer than the 10 electrodes used in acquiring the standard 12-lead ECG. Several such lead systems are in clinical use. They include: 1) the 5-electrode EASI lead system, 2) the 6-electrode reduced standard lead system, and 3) the 8-electrode Vectorcardiographic (Frank) lead system (see, e.g., Drew et al., "Practice Standards for Electrocardiographic Monitoring in Hospital Settings", Circulation vol. 110, pages 2721-46 (2004)). The cardiac ischemia detection apparatuses and techniques disclosed herein are readily applied to conventional 12-lead ECG (e.g. FIG. 2), modified 12-lead ECG (e.g. FIG. 3), and derived 12-lead ECG from various reduced-electrode configurations described above.

The term myocardial ischemia refers to a reduction in the supply of blood to the muscle cells of the heart. This occurs when the arterial conduit becomes limited in its ability to feed tissues with oxygen sufficient to meet their metabolic requirements. The main cause of myocardial ischemia is coronary artery disease. The effects of ischemia are reversible if the episode is limited in time. When an episode remains unrelieved, tissue cells begin to die and a myocardial infarction is the results.

With reference back to FIG. 1, after ventricular depolarization, normal myocardial cells are at nearly the same potential. Therefore in the absence of any cardiac pathology, the end of depolarization and the beginning of repolarization are normally isoelectric. On the ECG signal, this region is called the ST segment. It is defined as the region between the end of the S-wave, also called the J-point, and the beginning of the T-wave (see FIG. 1).

Ischemic and damaged tissue causes the cells of the myocardium to become either more or less excitable. This abnormal electrical characteristic change is most apparent in the repolarization phase. Since the ST segment of the ECG primarily reflects ventricular repolarization, the ischemia or cell damage is displayed as changes (depression or elevation) in the level of the ST segment.

The location of the ECG electrodes and the direction and magnitude of the ST change indicate the area of the heart at risk, and the possible extent of the damage. The probability of detecting ischemic episodes, and locating them, increases with the number of ECG leads employed, the appropriate choice of ECG leads, and correct lead placement.

The current standard of determining the ST segment measurement (see, e.g. Rautaharju et al., "AHA/ACCF/HRS Recommendations for the Standardization and Interpretation of the Electrocardiogram Part IV: The ST Segment, T and U Waves, and the QT Interval. Circulation", vol. 119, pages e241-e250 (2009)) is by measuring the voltage difference between the value at the J-point or a point 60 or 80 milliseconds (ms) after the J-point and the isoelectric baseline (see FIG. 1). The isoelectric baseline is either between the P- and Q-waves (the P-R interval) or in front of the P-wave (the T-P interval). ST segment measurement values can be reported in millivolt (mV), microvolt (uV) or millimeter (mm). (The latter measurement is arrived at because the standard ECG strips are normally plotted at a scale of 10 mm per 1 mV, thus 1 mm ST segment change represents a voltage change of 0.1 mV.) A positive value represents an ST elevation, and a negative value represents an ST depression. ST segment changes of greater than 1 mm (or 0.1 mV) are generally considered significant.

Acute coronary syndrome (ACS) refers to three types of coronary artery disease that are associated with sudden rupture of plaque inside the coronary artery, including unstable angina (UA), non-ST segment elevation myocardial infarction (NSTEMI), and ST segment elevation myocardial infarction (STEMI). The location of the blockage, the length of time that blood flow is blocked and the amount of damage that occurs determines the type of acute coronary syndrome. Myocardial infarction is a major cause of death and disability worldwide. In the United States alone, more than one million hospitalizations are required for ACS of which more than half are for acute myocardial infarction (AMI) including roughly two-thirds with NSTEMI and the rest with STEMI.

According to the current consensus document (Thygesen et al., "Joint ESC/ACCF/AHA/WHF Task Force for the Redefinition of Myocardial Infarction. Universal definition of myocardial infarction", J Amn Coll Cardiol vol. 50, pages 2173-95 (2007)) from the European Society of Cardiology (ESC)/American College of Cardiology Foundation (ACCF)/American Heart Association (AHA)/World Heart Federation (WHF), the STEMI criteria for the standard 12-lead ECG are: ST elevations measured at the J-point in two contiguous leads with value greater than or equal to 0.2 mV (or 2 mm) in men, or greater than or equal to 0.15 mV (or 1.5 mm) in women in leads V2, V3 and/or greater than or equal to 0.1 mV (or 1 mm) in other 10 leads. The 10 contiguous lead pairs are defined as: (aVL, I), (I, –aVR), (–aVR, II), (II, aVF), (aVF, III), (V1, V2), (V2, V3), (V3, V4), (V4, V5), (V5, V6). In this notation, note that –aVR=minus aVR. Criteria for right-side and posterior leads are provided in the AHA/ACCF/HRS Scientific Statement document (Wagner et al., "AHA/ACCF/HRS Recommendations for the Standardization and Interpretation of the Electrocardiogram Part VI: Acute Ischemia/Infraction", Circulation vol. 119, pages e262-e270 (2009)).

Current practice guidelines for managing patients with AMI are aimed to optimize care and outcome for these patients. For the STEMI patients, since the infarct-related artery is usually totally occluded, the treatment goal is to obtain normal coronary blood flow and interrupt the infarction as rapidly as possible. Effective reperfusion treatment options include intravenous thrombolytic therapy and percutaneous coronary intervention (PCI). Specifically, the current treatment guidelines (Antman et al., "2007 Focused Update of the ACC/AHA 2004 Guidelines for the Management of Patients with ST-Elevation Myocardial Infarction", J Am Coll Cardiol vol. 51, pages 210-247 (2008)) for the STEMI patients are: 1) for a hospital with PCI capability, treat with primary PCI within 90 minutes or first medical contact, and 2) for a hospital without PCI capability, treat with fibrinolytic therapy within 30 minutes of hospital presentation unless fibrinolytic therapy is contraindicated. Regardless of the mode of reperfusion, the overarching concept is to minimize total ischemic time, which is defined as the time from onset of symptoms of STEMI to initiation of reperfusion.

To effectively manage STEMI patients in order to achieve the treatment goals, a rapid and accurate diagnosis is essential. Because biochemical markers of AMI may not arise immediately after the onset of symptoms, the initial diagnosis and decision of reperfusion treatment are most often based on clinical symptoms and the standard 12-lead ECG as interpreted by on-site treating medical personnel. For patients presenting suggestive symptoms and obvious ST segment elevations that meet the current ESC/ACCF/AHA/WHF established acute STEMI guidelines, no further decision support is needed. However, for patients with less definitive ST segment changes, misinterpretation of the ECG by treating medical personnel can lead to diagnostic error and consequent non-optimal patient treatment.

In one study, emergency physicians blinded to biomarker results established the diagnosis of STEMI using admission ECGs with a high specificity of 99.7% (95% CI, 98%-99.9%), although sensitivity was low at 42% (95% CI, 32%-52%). See "2005 International Consensus Conference Part 5: Acute Coronary Syndromes", Circulation vol. 112, pages III55-III72 (2005). The ECG diagnosis of AMI could potentially be optimized by adding posterior thoracic and/or right-sided precordial leads; or by recording electrical potentials around the torso, termed body surface potential mapping (BSPM). However, emergency medical personnel are trained to perform ECG using the conventional 12-lead ECG configuration, and the use of other ECG configurations (especially ones requiring more than 12 leads) is likely to introduce delay in emergency treatment and/or potentially result in errors in data acquisition and/or interpretation.

An alternative approach for optimizing clinical usefulness of the ECG is to rearrange the available information from the standard leads. One example of this approach is using lead –aVR (minus aVR) instead of aVR to produce an "orderly" display of limb leads, analogous to the conventional orderly display of the standard chest leads. This method has been shown to improve the diagnosis of inferior and lateral myocardial infarcts.

Another study (Nimmermark et al., "The impact of numeric and graphic displays of ST-segment deviation levels on cardiologists' decisions of reperfusion therapy for patients with acute coronary occlusion", J Electrocardiol vol. 44, pages 502-508 (2011)) investigated the impact of adding numeric and/or graphic display of the ST measurement to the standard 12-lead ECG on cardiologists' decisions of reperfusion therapy for patients with either ST-segment depression or only borderline ST-segment elevation during PCI-induced acute ischemia. The graphic form chosen for presenting the ST-segment measurements is referred to as an "ST Map". Costa et al., "Method of Medical Monitoring", Int'l Appl. WO 2006/033038 A2, published 30 Mar. 2006.

Figure 4:
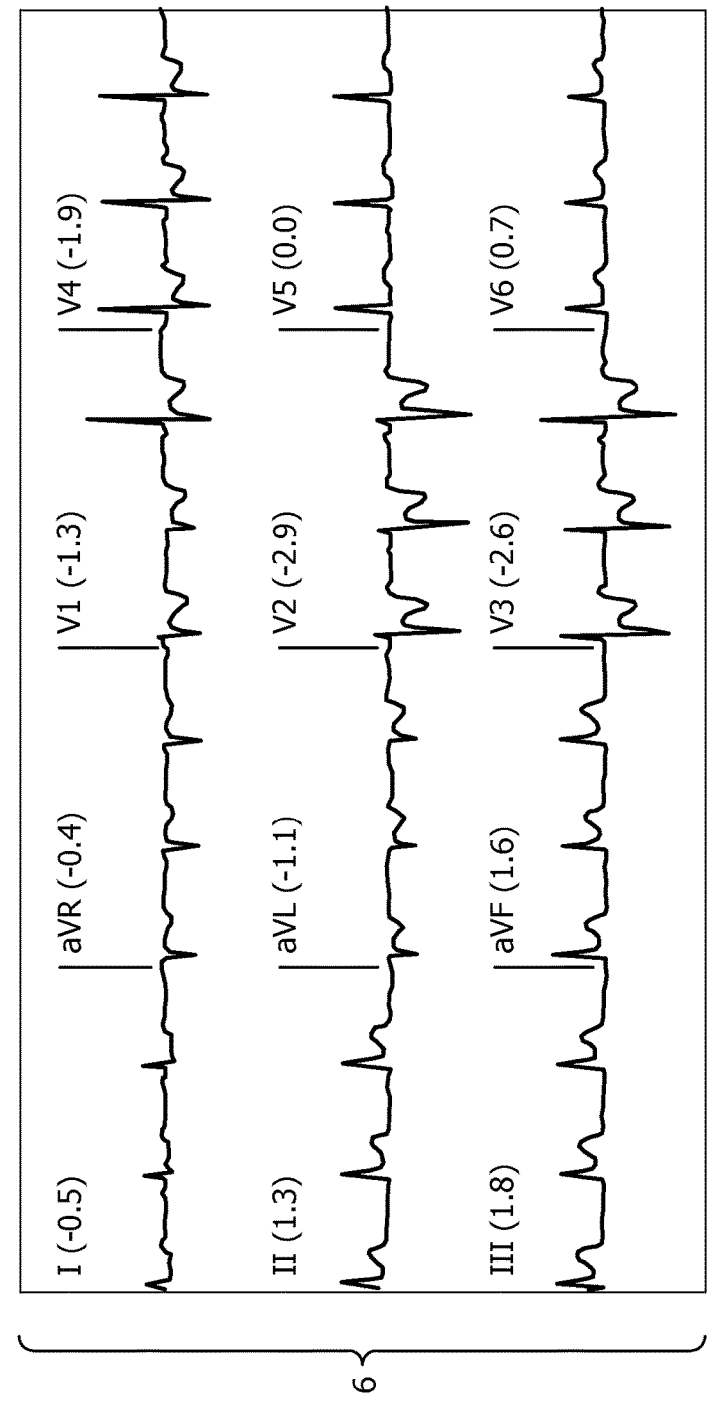
FIG. 4 shows an illustrative display for representing ECG data including ECG traces (upper window) and an ST Map (lower window).

With reference to FIG. 4, one suitable display includes the twelve ECG traces for the twelve leads in an upper window 6, and the ST Map in a lower window 8. The ST Map displays the quantitative ST-segment measurements of the six limb leads and the six chest leads in side-by-side frontal and transverse plane graphic presentations 10, 12 as shown in FIG. 4. The 3 concentric circles in each graphic presentation 10, 12 represent ST deviations of 1, 2, and 3 mm (positive or negative) with the center representing 0 mm. For each ECG lead, an axis is plotted through the center according to the spatial orientation of the specific lead. The frontal plane graphic presentation 10 includes axes for limb or augmented leads, namely leads I, II, aVF, III, aVR, and aVL (moving clockwise in the frontal plane presentation 10) in the illustrative 12-lead ECG case. The transverse plane graphic presentation 12 includes axes for precordial (i.e., chest) leads, namely leads V1, V2, V3, V4, V5, and V6 (moving counter-clockwise in the transverse plane presentation 12) in the 12-lead ECG case. The positive direction of the lead is indicated by a "+" sign next to the lead label. For each ST measurement, a point on the corresponding lead axis is indicated. The ST Map is completed by connecting these points to form a six-sided polygon, i.e., a (generally irregular) hexagon.

The results of the Nimmermark et al. study show that for ECGs that meet the STEMI criteria, the detection sensitivity was improved with the graphical ST Map presentation. However, the overall detection sensitivity was low. In addition, there was a wide variation in the interpretation among the practicing cardiologists who participated in the study.

Disclosed herein are methods and systems that are expected to provide improved accuracy in interpreting the ECG for ischemia identification. A graphical presentation is employed, in which both the ischemia criteria and the ST segment measurements to be tested are graphically presented simultaneously. The graphical presentation allows the violation of the ischemia criteria to be unambiguously visualized. To further ensure that such a condition will not be overlooked, additional graphical highlighting is provided. With this graphical approach, the detection of conditions that fulfill specified ischemia criteria is expected to be substantially enhanced, and the variation of individual interpretation for patients with borderline ST segment changes is expected to be reduced.

Figure 5:
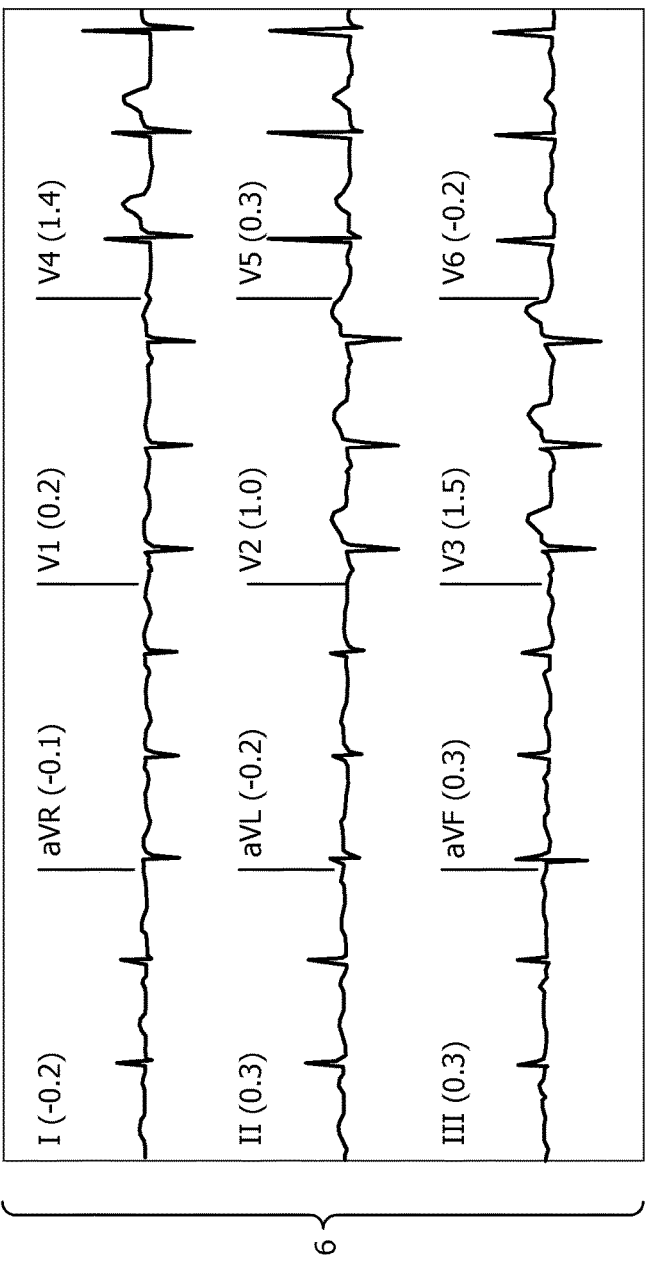
FIG. 5 shows an illustrative display for representing ECG data including ECG traces (upper window) and an ST Map with a highlighted graphical representation of an ischemia criteria area (lower window).

With reference to FIG. 5, an example of a suitable graphical presentation is shown. In this graphical presentation, the upper window 6 of FIG. 4 is retained in order to provide the "raw data", that is, the twelve ECG traces generated by the 12-lead ECG. However, the lower window 8 of FIG. 4 showing the ST Map comprising side-by-side frontal and transverse plane graphic presentations 10, 12 is replaced by a modified presentation window 18. The modified presentation shows side-by-side frontal and transverse plane graphic presentations 20, 22 with the ST values plotted to form a (irregular) hexagon, as in FIG. 4. However, the modified presentation additionally delineates an ischemia criteria area 24 denoting the portions of the planes 20, 22 in which an ST value would satisfy the ischemia criteria (e.g., the guideline STEMI criteria). The ischemia criteria areas are suitably delineated as shaded or colored areas. Additionally, the area enclosed by the plotted ST values is preferably delineated by shading or coloration. That is, the areas enclosed by the (generally irregular) hexagons in the case of 12-lead ECG are shaded or colored. This area is referred to herein as an ST area 26. When the STEMI criteria are met (as in the example of FIG. 5) the overlapping region 28 of the ST Map polygon (i.e., ST area) and the ischemia criteria area 24 is further highlighted by suitable coloration, shading, or so forth. In illustrative FIG. 5, the ischemia criteria area 24 is colored or shaded gray (as used herein, the term "color" encompasses black, white, and various shades of gray), the ST area 26 (defined by the irregular hexagons whose six vertices are six ST values) is shaded by crosshatching, and an overlapping region 28 of the ST Map polygon and the shaded ischemia criteria area is further highlighted by a lighter gray coloring or shading. As another example, in some embodiments, the overlapping region 28 of the ST Map polygon and the ischemia criteria area is highlighted by being colored red or another distinctive color. It is also contemplated to highlight the overlapping region 28 of the ST Map polygon and the ischemia criteria area by making it flashing or otherwise modulating its intensity over time.

The disclosed graphical presentation combining the ST Map with a graphical representation of the ischemia criteria area (and optional further highlighting of any overlap between the ST area and the ischemia criteria area) is referred to herein as an Ischemia Map. In embodiments in which the ischemia criteria represented by the ischemia criteria area is the guideline STEMI criteria, the Ischemia Map is also referred to herein as a STEMI Map. While the thresholds used in the current STEMI criteria are all positive values (ST elevation), in general ischemia criteria may also include negative ST values (ST depression). However, it should also be noted that the presence of an overlap between the ST area and the ischemia criteria area does not conclusively indicate that ischemia or STEMI is actually present in the patient. This is because ST values can be affected by many different conditions besides ischemia or STEMI. Accordingly, although the improved graphical representation (e.g., FIG. 5) enhances the ability of the cardiologist or other emergency treating medical personnel to detect indication of ischemia or STEMI in the ECG data of a patient, it is imperative that the cardiologist or other treating medical personnel interpret the ST information in the context of other available clinical information. By way of illustrative example, some of the non-ischemic causes of ECG changes that can mimic ischemia include: body position changes, drug effects (such as digitalis and diuretics), electrolyte imbalances (such as hypokalemia), conduction disturbances (including LBBB (Left Bundle Branch Block) and WPW (Wolff-Parkinson-White) syndrome), hypothermia, left ventricular hypertrophy, ventricular pacing, and old infarcts.

The illustrative examples herein employ 12-lead ECG for which there are six ST values forming a (generally irregular) hexagonal ST area in each of the frontal and transverse plane graphic presentations 20, 22. However, it will readily be appreciated that the approach can be extended to more leads, in which case the ST area may be other than hexagonal in shape. The terms "highlighting", "coloring", "coloration", "shading", and similar phraseology are to be understood as denoting any suitable delineation of an area, and suitably encompass coloring the area using a distinctive color (typically the preferred approach since human vision is strongly attracted to distinctive colors such as red, green, yellow, or so forth) or shading, crosshatching, or texturing the area (suitably used in conjunction with monochrome displays).

A suitable implementation for generating the disclosed Ischemia Map is as follows. The input information provided includes: ECG lead angles; patient gender; the ischemia criteria to be tested; and the ST measurements. The ECG lead angles may be explicit input values, or may be assumed values (i.e., not explicitly input), in which case pre-configured default values for the 12-lead ECG or other employed ECG configuration are used. Patient gender is also optional information if the gender is not provided then a pre-configured default gender setting can be used. The ischemia criteria to be tested may also optionally be a default value, e.g. the system may be pre-configured to test the standard guideline STEMI criteria (or some other standard ischemia criteria). The ST measurements include twelve ST measurements for a 12-lead ECG, but optionally may include more or fewer ST measurements if an ECG configuration other than the standard 12 lead configuration is employed (e.g., if additional right-side leads are included then more than twelve ST measurements are input). Given the foregoing inputs, the Ischemia Map generation is suitably performed as follows. In a first step, the lead angles as specified (either explicitly input or default values) are used to generate the frontal plan and transverse plan plots. The concentric circles, which represent the scales of the ST deviations, can be pre-defined using fixed scales, automatically scaled according to the range of the input ST measurements, or user adjustable (by specifying the desired scales). In a second step, the ischemia criteria as specified (either explicitly selected or a default ischemia criteria, e.g. the guideline STEMI criteria) are used to delineate the ischemia criteria areas on the frontal and transverse plans. If gender information is provided then these areas are gender-specific, i.e. either male if the patient is specified to be male or female if the patient is specified to be female). If no gender is input, then a pre-specified default setting is used. In a third step, each input ST measurement is marked as a point on its corresponding lead axis (defined by the lead angle as specified for that lead). The ST area is delineated by connecting the ST measurement points (optionally plus the 0 point as described hereafter) to form a closed polygon. In a fourth step, the ST measurements are checked against the ischemia criteria. If the ST measurements fulfill the ischemia criteria, the overlapping area of the ST area and the ischemia criteria area is highlighted. Finally, in a fifth "iteration" step the third and fourth steps are repeated for each new set of ST measurements.

In a conventional ST Map (see Costa et al., "Method of Medical Monitoring", Int'l Appl. WO 2006/033038 A2, published 30 Mar. 2006), the polygon in the ST Map is formed by connecting the ST measurements (e.g., connecting six ST values to form a hexagon for conventional 12 lead ECG). The 0 point is not included unless it happens to be one of the actual ST measurements.

Figure 6:
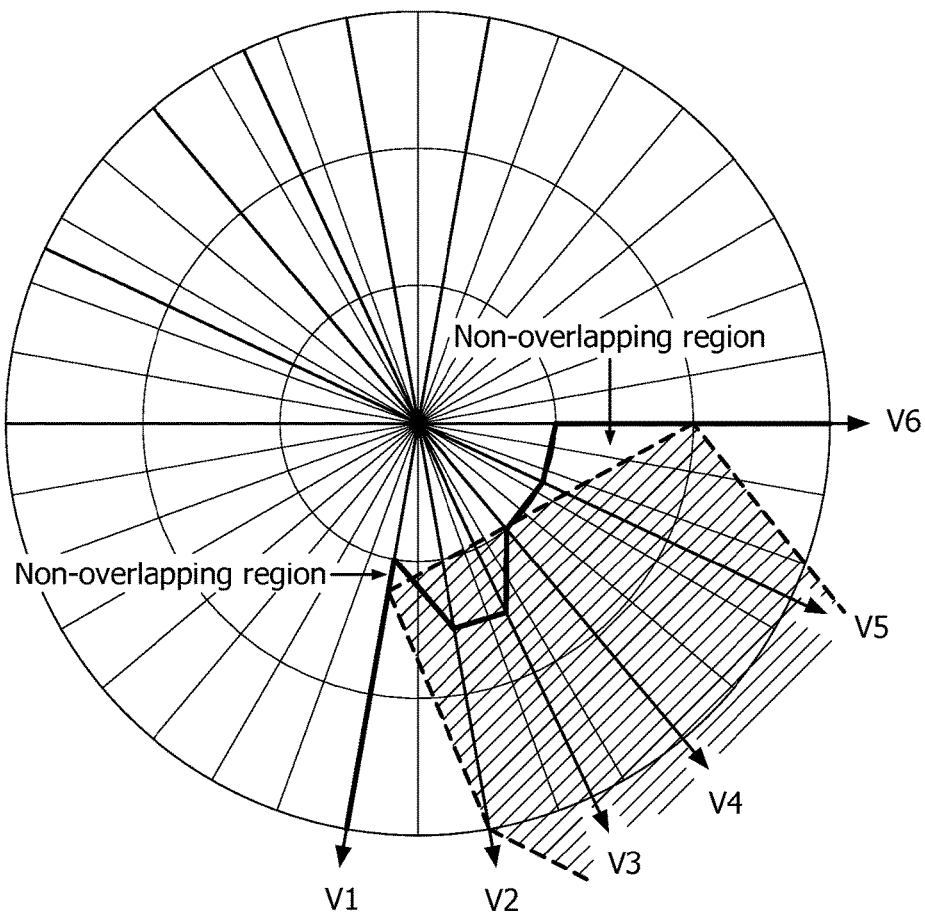
FIG. 6 shows an ST Map in which the 0 point is not included in the polygon connecting the ST measurements.

However, as illustrated in FIG. 6, this can create difficulties in interpreting the Ischemia Map. FIG. 6 shows an Ischemia Map including lines forming the polygon from the ST measurements (the dashed lines in FIG. 6) and lines forming the ischemia criteria area specified by the ischemia criteria (solid lines in FIG. 6). The overlapping region is covered by dotted slanted hatching in FIG. 6. It will be noticed in the example of FIG. 6 that non-overlapping regions can occur if the ST area does not include the 0 point as one of the ST measurements. These non-overlapping areas can complicate the visual interpretation of the Ischemia Map, which is intended to be rapidly visually assessed by clinical personnel in an emergency situation. Note that in FIGS. 6-9 the additional lines crossing through the center (0 point) of the ST Map are the 10-degree grid lines.

Figure 7:
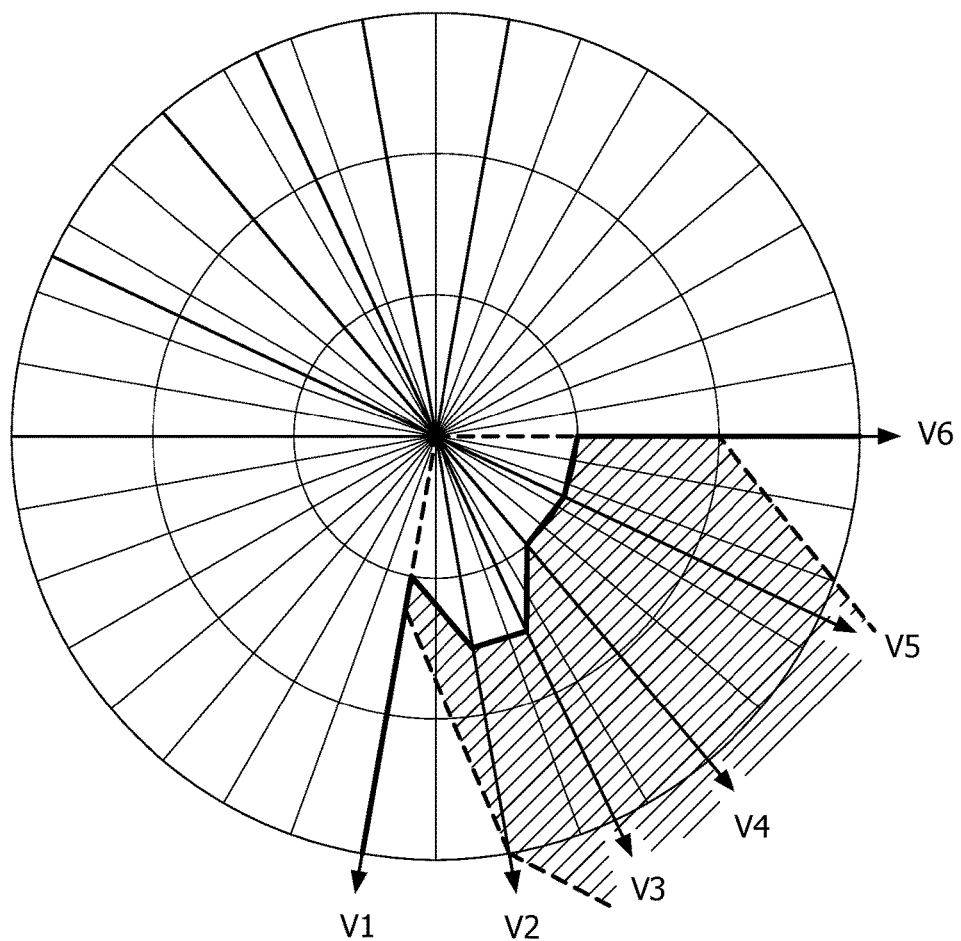
FIG. 7 shows the ST Map of FIG. 6 but with the 0 point included in the polygon connecting the ST measurements.

With reference to FIG. 7, improved readability can be achieved by always including the 0 point when forming the ST area. In FIG. 7 the polygon connecting the ST measurements (and also connecting the zero point in FIG. 7) is shown by dashed lines, while the lines forming the ischemia criteria area specified by the ischemia criteria are shown in solid lines.

Figure 8:
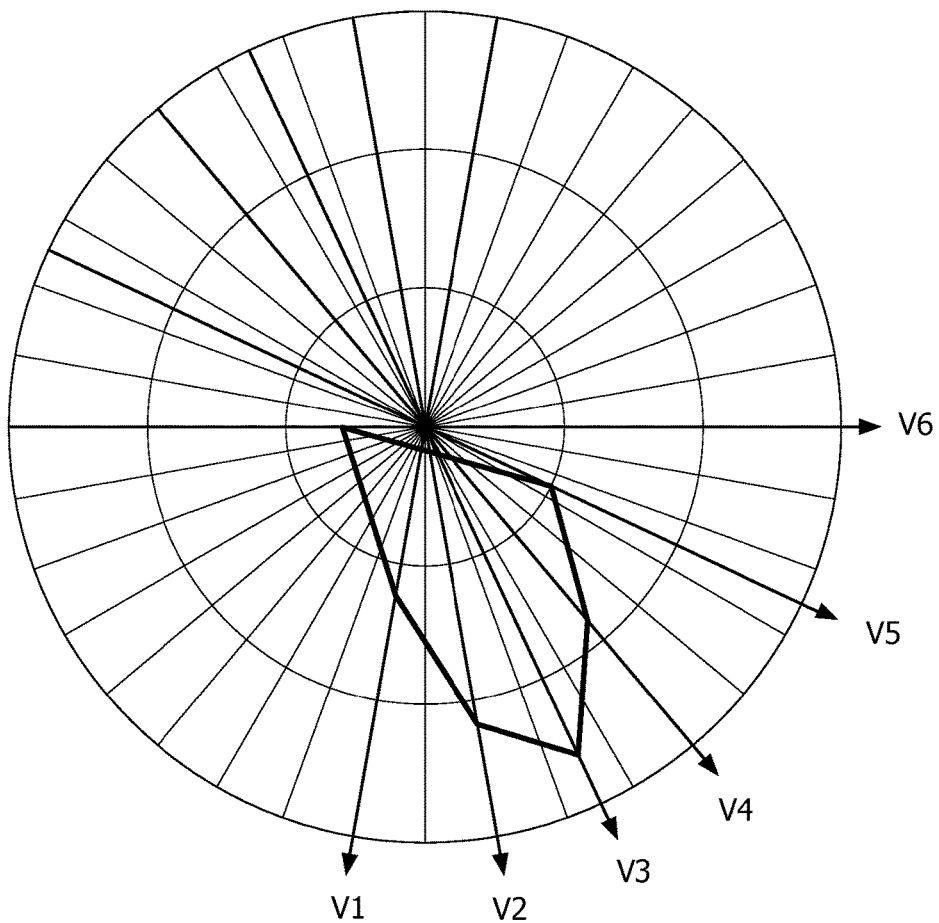
FIG. 8 shows another ST Map in which the 0 point is not included in the polygon connecting the ST measurements.
Figure 9:
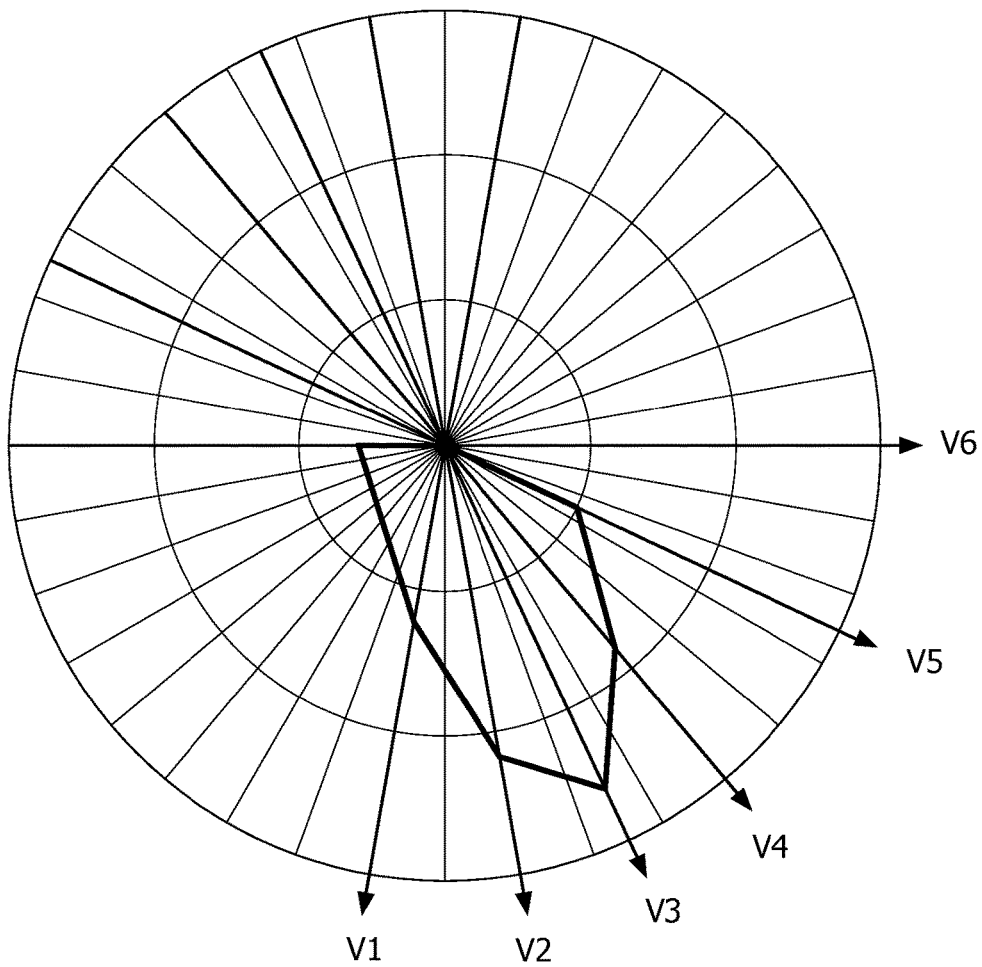
FIG. 9 shows the ST Map of FIG. 8 but with the 0 point included in the polygon connecting the ST measurements.

With reference to FIGS. 8 and 9, the exclusion/inclusion of the zero point is illustrated using conventional ST Map without delineating the ischemia criteria area. FIG. 8 shows the ST area without including the 0 point in the polygon, and FIG. 9 shows the (modified) ST area where the 0 point is included.

As already noted, the disclosed Ischemia Mapping approach is suitably employed for ECG configurations other than the standard 12 lead ECG. Some discussion of modified or alternative ECG configurations follows.

While there is universal agreement of the angles (30 degrees between leads) of the six frontal plan limb leads, there are no standardized angles for the presentation of the six transverse chest leads. Five different sets of placements for the chest leads are listed in Table 2. In the table, the horizontal lead pointing to the right is designated as 0 degree. Lead angles in the clockwise direction are defined as positive.

TABLE 2

Several sets of chest lead presentation

| | Lead Angles | | | | | | | | |
|---|---|---|---|---|---|---|---|---|---|
| | V6 | V5 | V4 | V3 | V2 | V1 | V3R | V4R | V5R |
| Reference [7] | −30 | 0 | 30 | 60 | 90 | 120 | — | — | — |
| WO 2006/033038 | 0 | 30 | 60 | 75 | 90 | 120 | — | — | — |
| WO 2010/037400 | −10 | 15 | 40 | 65 | 90 | 115 | | | |
| 20° Between Leads | 0 | 20 | 40 | 60 | 80 | 100 | 120 | 140 | 160 |
| Reference [10] | 0 | 25 | 50 | 65 | 80 | 100 | 115 | 130 | 155 |

[7] Nimmermark et al., J Electrocardiol vol. 44, pages 502-508 (2011);
[10] Goldman MJ. Principles of Clinical Electrocardiography. Los Altos, CA: Lange Medical Pubns, 7$^{th}$ edition, 1970.

While all the sets shown in Table 2 are acceptable for 12-lead ST Map presentation, some sets are also suitable for supporting additional right-side leads. Because the right-side leads V3R, V4R, and V5R are placed on the right side chest as mirror image to the standard precordial electrodes V3, V4, and V5, respectively, sets with leads V1 and V2 symmetrical around the 90-degree direction are required to support these right-side leads. Two sets that support these additional leads are shown with their right-side electrode placement locations. The preferred choice is the last set because it reflects more closely to the physical locations of the electrode placement.

In the following, several examples of the present invention are illustrated using the guideline STEMI criteria.

Figure 10:
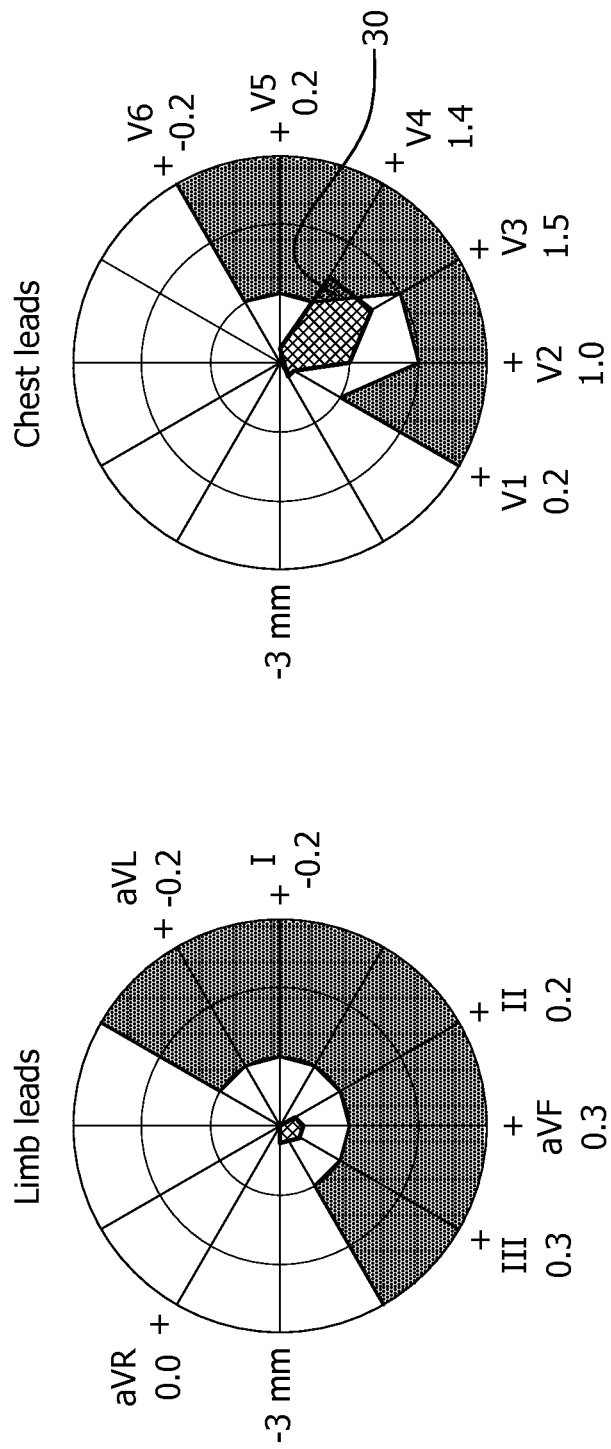
FIG. 10 shows an illustrative example of an ST Map for ECG data that do not satisfy the ischemia criteria.

With reference to FIG. 10, the STEMI criteria for the male gender is shown delineated by gray shading, and the ST area is shown delineated by crosshatching. In the example of FIG. 10, although there is a region 30 in the transverse plane in which the ST area overlaps with the STEMI region, the overlapping region 30 is not highlighted (so as to indicate a region satisfying the STEMI criteria) because only one lead (V4) exceeds the STEMI limits. To fulfill the STEMI criteria two contiguous leads both exceeding their corresponding limits are required.

Figure 11:
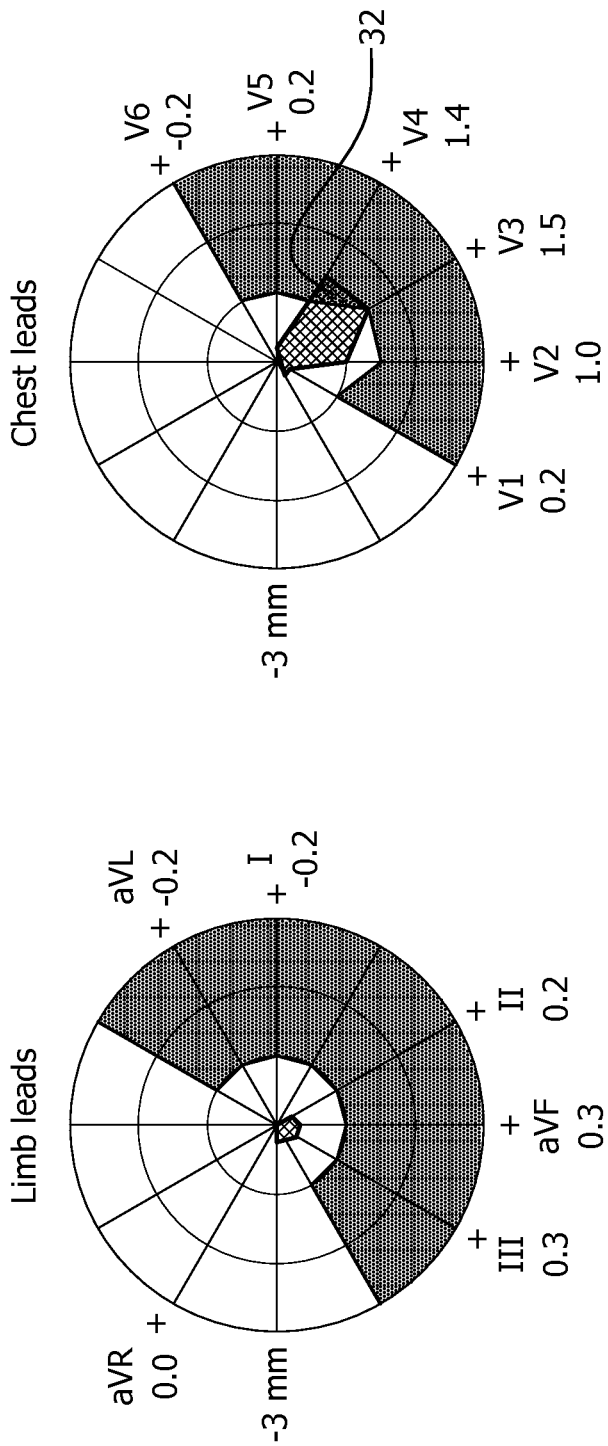
FIGS. 11-14 shows illustrative examples of ST Map for ECG data that satisfy the ischemia criteria, with a highlighted graphical representation of the ischemia criteria area in each ST Map.

With reference to FIG. 11, the same ST measurements are shown, but in conjunction with the STEMI criteria for the female gender. Again, the STEMI criteria area is delineated by gray shading and the ST area is delineated by crosshatching. Here, the ST measurements meet the STEMI criteria for two contiguous leads, namely for the two contiguous leads V3 and V4. This is because for female patients the STEMI limits are lower for leads V2 and V3. Thus, FIG. 12 shows the corresponding overlapping area 32 highlighted (by a lighter shade of gray in FIG. 12; in embodiments employing a color monitor, highlighting in red or another distinctive color can be advantageous).

Further examples are shown in FIGS. 12-14, where yet again in each case the STEMI criteria area is delineated by gray shading, the ST area is delineated by crosshatching, and any overlapping area satisfying the STEMI criterion is highlighted by lighter gray coloration as compared with the gray shading of the STEMI criteria area.

Figure 12:
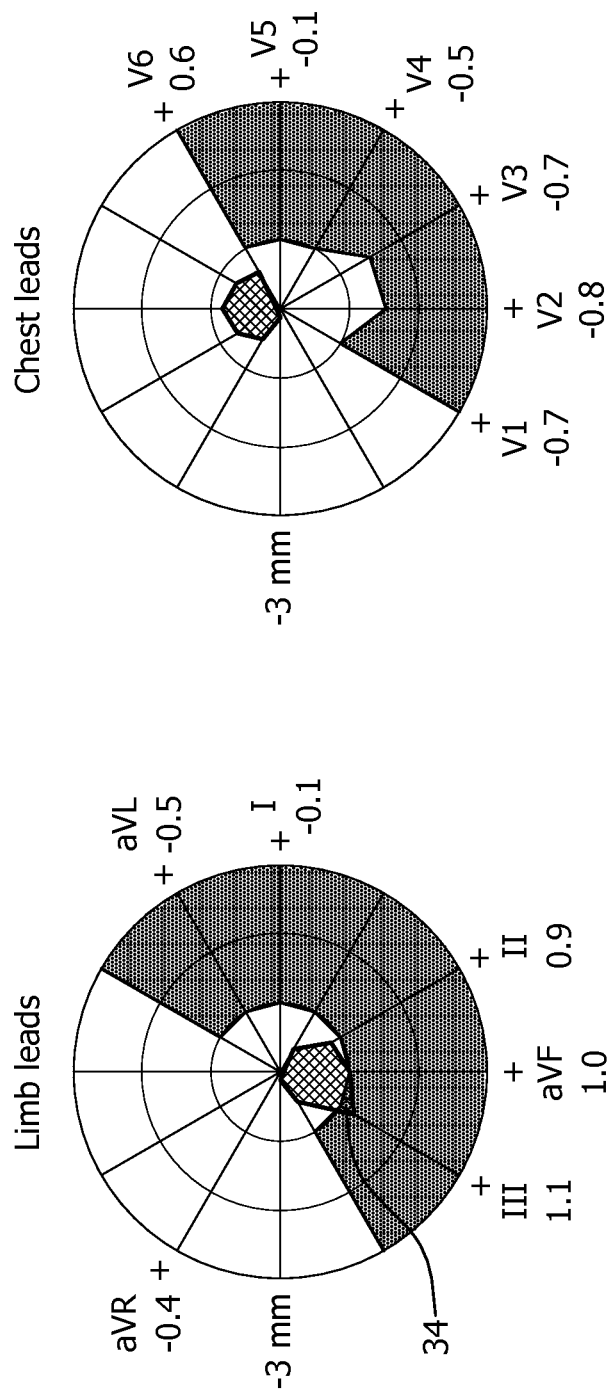

With reference to FIG. 12, a case is shown in which two contiguous limb leads (III and aVF) both exceed the STEMI limits and the corresponding overlapping region 34 in the frontal plane is highlighted (in lighter gray coloration in FIG. 12).

Figure 13:
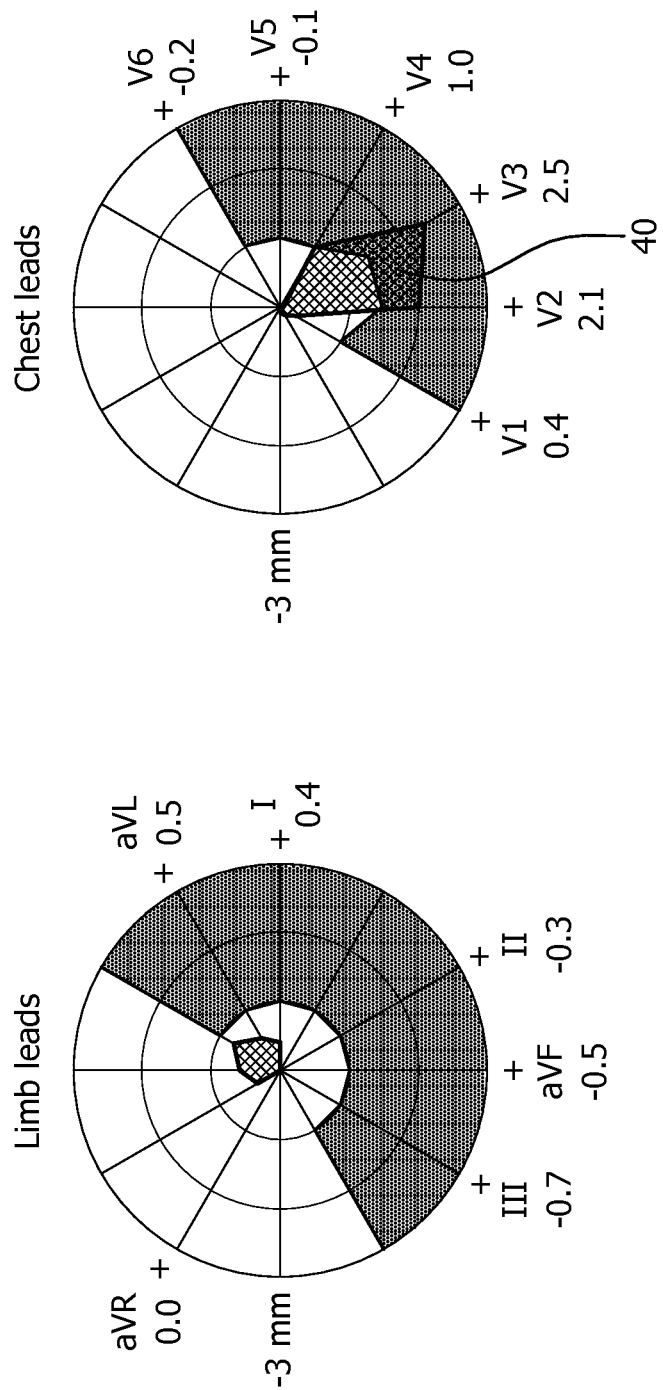
Figure 14:
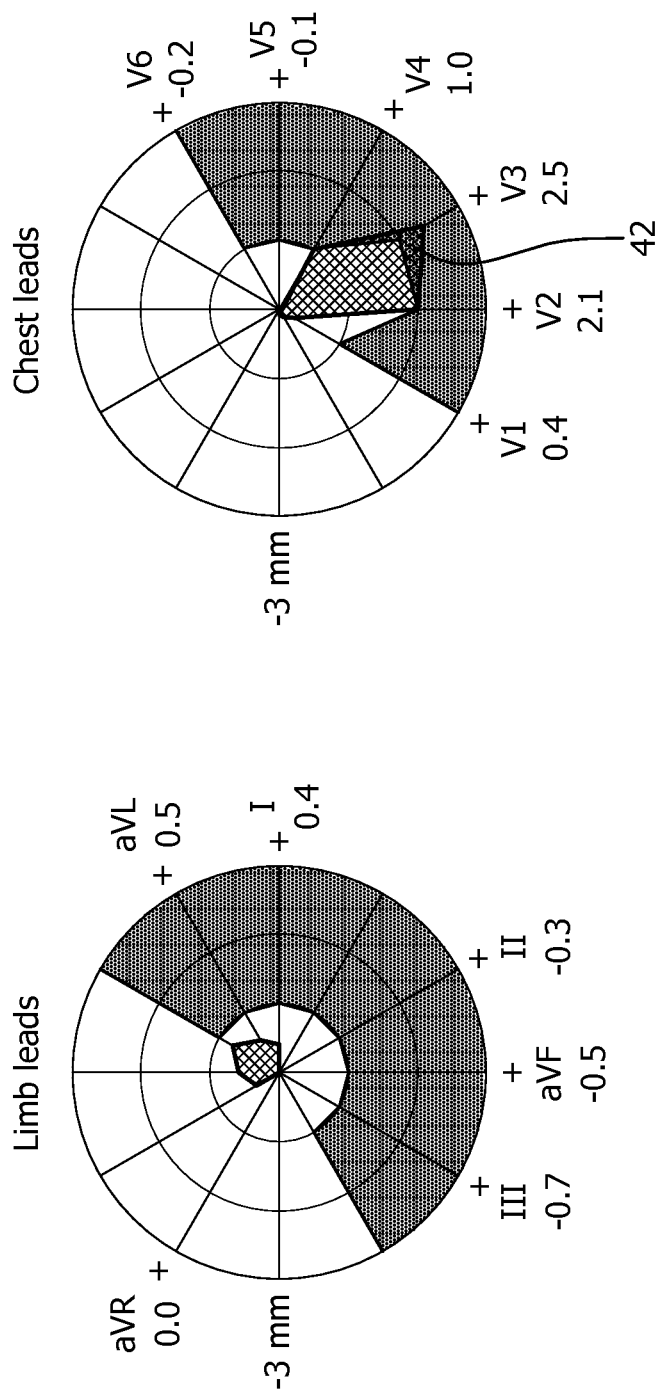

With reference to FIGS. 13 and 14, an example is shown in which the ECG is STEMI (i.e., the ST values satisfy the STEMI criteria) regardless the patient's gender is male or female. FIG. 13 shows the case for female gender STEMI criteria, while FIG. 14 shows the case for male gender STEMI criteria. The STEMI criteria are satisfied by the large ST segment elevation associated with the chest leads V2 and V3 in this example. Consequentially, an overlapping area 40 is highlighted in the (female) example of FIG. 13, and an overlapping area 42 is highlighted in the (male) example of FIG. 14.

When the ischemia criteria are not satisfied by the measured ST values, there may still be some overlap between the ST area and the ischemia criteria area, as illustrated in FIG. 10. In such cases, the overlap is not highlighted.

On the other hand, when the ischemia criteria are satisfied by the measured ST values, there is always some overlap between the ST area and the ischemia criteria area, and this overlap is preferably shown in red or otherwise highlighted. The illustrative examples show cases in which this overlap occurs in the transverse plane, which has axes representing electrocardiograph precordial leads (e.g., FIGS. 11, 13, and 14). The illustrative examples also include one case in which this overlap occurs in the frontal plane, which has axes representing electrocardiograph limb or augmented leads (FIG. 12). The skilled artisan will readily recognize that in many ischemia cases, the overlap may be present in both the transverse and frontal planes.

With reference to FIG. 15, a suitable instrument performing the disclosed cardiac ischemia detection technique is disclosed. An electronic patient monitoring device 50 is suitably an ECG based device including (as illustrated) or receiving data from an ECG acquisition sub-system 52 and configured to provide ST segment analysis for ischemia detection. By way of illustrative example, the electronic patient monitoring device 50 may suitably be a bedside monitor, telemetry monitor, defibrillator, cardiograph, Holter system, stress testing system, or so forth. The electronic patient monitoring device 50 includes a patient configuration user interface 54 via which the cardiologist, nurse, or other operator enters relevant information 56 such as a selection of the ischemia criteria (suitably chosen from an ischemia criteria database 58, or alternatively a default ischemia criteria can be employed), patient gender, and ECG lead angles (again, these may be default values as in the illustrative user entry dataset 56). In the illustrative example, the standard 12 lead ECG STEMI criteria of Table 3 is selected as the ischemia criteria.

TABLE 3

Threshold Values of the Standard 12-Lead ECG STEMI Criteria

| Leads | Male | Female |
|---|---|---|
| V2, V3 | ≥0.2 mV | ≥0.15 mV |
| All other leads | ≥0.1 mV | ≥0.1 mV |

The electronic patient monitoring device 50 includes an electronic data processor 60 (e.g., a digital microprocessor, microcontroller, or so forth) configured to perform the disclosed cardiac ischemia detection and alerting functionality. Initially, an ischemia area calculator 62 computes the ischemia criteria area for the frontal and transverse plane graphic presentations. This calculation entails identifying the threshold along each ECG lead angle pair (e.g., as given in Table 3 for the standard STEMI criteria) and defining the ischemia criteria area as all points extending radially outward from these thresholds. (By way of illustrative example, the 12 Lead ECG STEMI criteria for a male patient is shown in FIG. 10, and for a female patient is shown in FIG. 11. This is done at the initiation of patient monitoring or, alternatively, the ischemia criteria lead area may be pre-calculated and stored and then retrieved at the initiation of patient monitoring.

The patient monitoring is performed as an iterative loop 70. An ST values calculator 72 computes the ST values for the leads (e.g., twelve ST values for a 12 lead ECG configuration) and an ST area calculator 74 computes the ST area. For the 12 lead ECG the ST area is hexagonal (e.g., see FIG. 8) or seven-sided if the 0-point is explicitly included (e.g., see FIG. 9). In parallel, an ischemia criteria evaluator evaluates the ST values to determine whether the ischemia criteria has been satisfied (i.e., whether the ischemia criteria is violated). If so, then a trigger signal 78 is sent to an overlap calculator 80 which computes the overlap between the ST area and the ischemia criteria area. An Ischemia Map rendering engine 82 then computes the Ischemia Map including the ST area output by the calculator 74, the ischemia criteria area output by the calculator 62 (or which was precomputed and retrieved from memory), and any overlap area output by the calculator 80. The ST area, ischemia criteria area, and any overlap area are suitably rendered in distinctive colors as already described. The rendering is suitably displayed on a display device 84 (e.g., LCD screen) of the electronic patient monitoring device 50 and/or printed on a printing device. The iterative loop 70 is re-executed each time the ECG acquisition sub-system 52 and ST values calculator 72 generate a new set of ST values. (Alternatively, the updates can be done less frequently, and optionally the user interface 54 may provide a "pause" button or the like in order to freeze the display so that the cardiologist or other treating medical personnel can more carefully view a static display of the Ischemia Map).

It is also to be appreciated that the disclosed approaches for performing cardiac ischemia detection and alerting are suitably embodied by a non-transitory storage medium storing instructions executable by an electronic data processor (e.g., processor 60) to perform the disclosed cardiac ischemia detection and alerting. For example, the non-transitory storage medium may be: a hard disk or other magnetic storage medium; a random access memory (RAM), read-only memory (ROM), flash memory or other electronic storage medium; a DVD or other optical storage medium; or so forth.

It is also noted that in some contemplated embodiments the ST area and ischemia criteria area are displayed without highlighting the (possibly) ischemia-indicative overlap (if any) between the ST area and the ischemia criteria area. While this approach has the disadvantage of not providing the attention-grabbing highlighting (e.g., in red) of the (possibly) ischemia-indicative overlap area, it has the advantage of removing the relatively computationally intensive components 76, 80 of the system of FIG. 15.

In embodiments that include highlighting of the (possibly) ischemia-indicative overlap (if any), it will further be appreciated that the presence of the (possibly) ischemia-indicative overlap may be accompanied by an audible alarm emanating from the electronic patient monitoring device 50, and/or a flashing light mounted on the electronic patient monitoring device 50 or elsewhere. Referencing FIG. 15, such an audible or flashing alarm is suitably triggered by the same trigger signal 78 that initiates calculation of the (possibly) ischemia-indicative overlap.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. An electronic patient monitoring device comprising:
   an electrocardiograph system configured to acquire electrocardiographic data for a set of electrocardiograph leads;
   a display device;
   an electronic data processing device configured to:
      compute ST values from the electrocardiographic data;
      generate and display, on the display device, an ST Map plotting the ST values;
      superimpose, on the ST Map displayed on the display device, a rendering of an ischemia criteria area representing an ischemic criteria, wherein the ischemia criteria includes thresholds for leads of the set of electrocardiographic leads and the ischemia criteria area is bounded by the thresholds and extends radially outward from the thresholds;
      determine whether ST values of the ST Map satisfy the ischemia criteria; and
      conditional on the ST values of the ST Map satisfying the ischemia criteria, compute an overlap between (1) an ST area delineated by the ST values of the ST Map and (2) the ischemia criteria area and highlight the overlap on the ST Map displayed on the display device.

2. The electronic patient monitoring device of claim 1, wherein the ST Map further plots the 0 point value and the ST area is further delineated by the 0 point value.

3. The electronic patient monitoring device of claim 1, wherein the ST area is displayed on the ST Map in a first color, the ischemia criteria area is superimposed on the ST Map in a second color different from the first color, and the overlap, if highlighted, is highlighted in a third color different from the first and second colors.

4. The electronic patient monitoring device of claim 1, wherein the ST area is displayed on the ST Map in a first shading or crosshatching, the ischemia criteria area is superimposed on the ST Map in a second shading or crosshatching different from the first shading or crosshatching, and the overlap, if highlighted, is highlighted in a third shading or crosshatching different from the first and second shadings or crosshatchings.

5. The electronic patient monitoring device of claim 1, wherein the ischemia criteria comprise the guideline STEMI criteria.

6. The electronic patient monitoring device of claim 1, wherein the electronic data processing device is further configured to:
   select a gender-appropriate ischemia criteria thresholds for selected leads of the set of electrocardiograph leads;
   wherein the superimposed rendering of the ischemia criteria area represents the gender-appropriate ischemia criteria.

7. The electronic patient monitoring device of claim 1, wherein the electrocardiograph system is one of: a 12 lead electrocardiograph system, a Mason-Like electrocardiograph system, an EASI electrocardiograph system, a reduced standard lead electrocardiograph system, and a Vectorcardiographic electrocardiograph system.

8. A method comprising:
   compute ST values from electrocardiographic data;
   computing a polygonal ST area in a plane, the polygonal ST area having vertices defined by the computed ST values on axes representing electrocardiograph leads, wherein the computing is performed by an electronic data processing device;
   displaying a rendering of the polygonal ST area in the plane together with an ischemia criteria area representing an ischemia criteria in the plane;
   determining whether the measured ST values satisfy the ischemia criteria wherein the determining is performed by the electronic data processing device; and
   conditional upon determining that the measured ST values satisfy the ischemia criteria, highlighting an overlap between the polygonal ST area and the ischemia criteria area in the rendering.

9. The method of claim 8, wherein the highlighting includes displaying the overlap in red.

10. The method of claim 8, wherein the highlighting includes displaying the overlap in a distinctive color that is different from colors used in displaying the polygonal ST area and the ischemia criteria area.

11. The method of claim 8, further comprising:
    conditional upon determining that the measured ST values do not satisfy the ischemia criteria, not highlighting any overlap between the polygonal ST area and the ischemia criteria area in the rendering.

12. The method of claim 8, wherein the measured ST values are acquired from a subject, the method further comprising:
    selecting the ischemia criteria based on gender of the subject from a group consisting of (1) a male ischemia criteria and (2) a female ischemia criteria.

13. The method of claim 8, wherein the polygonal ST area further has a vertex defined by a zero point in the plane where the axes representing electrocardiograph leads meet.

14. The method of claim 8, wherein the plane includes a frontal plane with axes representing electrocardiograph limb or augmented leads and a transverse plane with axes representing electrocardiographic chest leads, and wherein:
    the computing includes:
       computing a frontal polygonal ST area in the frontal plane having vertices defined by measured ST values on the axes representing electrocardiograph limb or augmented leads and
       computing a transverse polygonal ST area in the transverse plane having vertices defined by measured ST values on the axes representing electrocardiograph chest leads, and
    the displaying includes:
       displaying a rendering of the frontal polygonal ST area in the frontal plane together with a frontal ischemia criteria area representing the ischemia criteria in the frontal plane and
       displaying a rendering of the transverse polygonal ST area in the transverse plane together with a transverse ischemia criteria area representing the ischemia criteria in the transverse plane.

15. The method of claim 8, wherein the ischemia criteria includes thresholds for leads of the set of electrocardiographic leads and the ischemia criteria area is bounded by the thresholds and extends radially outward from the thresholds.

16. A non-transitory storage medium storing instructions executable by an electronic data processing device perform a method including:

compute ST values from electrocardiographic data;

computing a frontal polygonal ST area in a frontal plane wherein the frontal polygonal ST area has vertices defined by the computed ST values on axes representing electrocardiograph limb or augmented leads;

computing a transverse polygonal ST area in a transverse plane wherein the transverse polygonal ST area has vertices defined by measured ST values on axes representing electrocardiograph precordial leads;

displaying a frontal plane graphic presentation including the frontal polygonal ST area and an ischemia criteria area representing the portion of the frontal plane in which an ST value would satisfy the ischemia criteria;

displaying a transverse plane graphic presentation including the transverse polygonal ST area and an ischemia criteria area representing the portion of the transverse plane in which an ST value would satisfy the ischemia criteria;

determining whether the measured ST values satisfy the ischemia criteria, and conditional upon determining that the measured ST values satisfy the ischemia criteria, highlighting an overlap between at least one of (1) the front polygonal ST area and the ischemia criteria area representing the ischemia criteria in the frontal plane and (2) the transverse polygonal ST area and the ischemia criteria area representing the ischemia criteria in the transverse plane.

17. The non-transitory storage medium of claim 16, wherein the highlighting includes displaying the overlap in a distinctive color that is different from colors used in displaying the polygonal ST area and the ischemia criteria area.

18. The non-transitory storage medium of claim 16, wherein the electronic data processing device is further programmed to:

conditional upon determining that the measured ST values do not satisfy the ischemia criteria, not highlight any overlap between the polygonal ST area and the ischemia criteria area in the rendering.

19. The non-transitory storage medium of claim 16, wherein the ischemia criteria includes thresholds for leads of the set of electrocardiographic leads and the ischemia criteria area is bounded by the thresholds and extends radially outward from the thresholds.

* * * * *